US009797859B2

(12) United States Patent
Carpenter

(10) Patent No.: US 9,797,859 B2
(45) Date of Patent: Oct. 24, 2017

(54) METHODS OF USING INFORMATION FROM RECOVERY PULSES IN ELECTROCHEMICAL ANALYTE MEASUREMENTS AS WELL AS DEVICES, APPARATUSES AND SYSTEMS INCORPORATING THE SAME

(71) Applicant: Roche Diabetes Care, Inc., Indianapolis, IN (US)

(72) Inventor: Scott E. Carpenter, Pendleton, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 230 days.

(21) Appl. No.: 14/851,944

(22) Filed: Sep. 11, 2015

(65) Prior Publication Data
US 2016/0003765 A1    Jan. 7, 2016

Related U.S. Application Data

(63) Continuation of application No. PCT/EP2014/054943, filed on Mar. 13, 2014.
(Continued)

(51) Int. Cl.
*G01N 27/327* (2006.01)
*A61B 5/145* (2006.01)
(Continued)

(52) U.S. Cl.
CPC ....... *G01N 27/3274* (2013.01); *A61B 5/1486* (2013.01); *A61B 5/1495* (2013.01);
(Continued)

(58) Field of Classification Search
CPC .................... G01L 27/327–27/3274
(Continued)

(56) References Cited

U.S. PATENT DOCUMENTS

2003/0060692 A1    3/2003  Ruchti et al.
2004/0157339 A1    8/2004  Burke et al.
(Continued)

FOREIGN PATENT DOCUMENTS

EP    1156324 A1    11/2001
EP    2042865 A2    4/2009
(Continued)

OTHER PUBLICATIONS

Gunasingham; et al., "Pulsed amperometric detection of glucose using a mediated enzyme electrode", Journal of Electroanalytical Chemistry and Interfacial Electrochemistry, Jul. 25, 1990, vol. 287, No. 2, pp. 349-362.

*Primary Examiner* — Bach Dinh

(57) ABSTRACT

Methods are disclosed for measuring an analyte concentration in a fluidic sample. Such methods allow one to correct and/or compensate for confounding variables such as temperature before providing an analyte concentration. The measurement methods use response information from a test sequence having at least one DC block, where the DC block includes at least one excitation pulse and at least one recovery pulse, and where a closed circuit condition of an electrode system is maintained during the at least one recovery pulse. Information encoded in the at least one recovery pulse is used to correct/compensate for temperature effects on the analyte concentration. Also disclosed are devices, apparatuses and systems incorporating the various measurement methods.

10 Claims, 10 Drawing Sheets

Related U.S. Application Data

(60) Provisional application No. 61/798,383, filed on Mar. 15, 2013.

(51) Int. Cl.
   *A61B 5/1473* (2006.01)
   *A61B 5/1486* (2006.01)
   *A61B 5/1495* (2006.01)

(52) U.S. Cl.
   CPC ...... *A61B 5/14532* (2013.01); *A61B 5/14735* (2013.01); *A61B 2560/0223* (2013.01); *A61B 2560/0252* (2013.01)

(58) Field of Classification Search
   USPC ..... 204/403.01–403.15; 205/777.5–778, 792
   See application file for complete search history.

(56) References Cited

U.S. PATENT DOCUMENTS

| | | |
|---|---|---|
| 2005/0279631 A1 | 12/2005 | Celentano |
| 2007/0102292 A1 | 5/2007 | Dreibholz et al. |
| 2009/0030641 A1 | 1/2009 | Fjield et al. |
| 2009/0292186 A1* | 11/2009 | Xu .................... A61B 5/14532 600/316 |
| 2010/0170807 A1* | 7/2010 | Diebold ............ G01N 27/3274 205/792 |
| 2013/0277234 A1* | 10/2013 | Burke ................ G01N 27/3274 205/777.5 |

FOREIGN PATENT DOCUMENTS

| | | |
|---|---|---|
| EP | 2138841 A2 | 12/2009 |
| EP | 2261646 B1 | 7/2015 |
| WO | 9932881 A1 | 7/1999 |
| WO | 0121827 A1 | 3/2001 |
| WO | 03060154 A2 | 7/2003 |
| WO | 2006109279 A2 | 10/2006 |
| WO | 2007100651 A1 | 9/2007 |
| WO | 2008036516 A1 | 3/2008 |
| WO | 2009075951 A1 | 6/2009 |
| WO | 2012134890 A1 | 10/2012 |

* cited by examiner

METHODS OF USING INFORMATION FROM RECOVERY PULSES IN ELECTROCHEMICAL ANALYTE MEASUREMENTS AS WELL AS DEVICES, APPARATUSES AND SYSTEMS INCORPORATING THE SAME

CROSS-REFERENCE TO RELATED APPLICATIONS

This patent application is a continuation of Int'l Patent Application No. PCT/EP2014/054943 (filed 13 Mar. 2014), which claims priority to and the benefit of U.S. Provisional Patent Application No. 61/798,383 (filed 15 Mar. 2013). Each patent application is incorporated herein by reference as if set forth in its entirety.

TECHNICAL FIELD

This disclosure relates generally to mathematics and medicine, and more particularly, it relates to methods of electrochemically measuring an analyte in a fluidic sample based upon response information from a test sequence having at least one direct current (DC) block, where the DC block includes a pulsed sequence having at least one recovery pulse.

BACKGROUND

Many analyte measurement systems, such as self-monitoring blood glucose (SMBG) systems, clinical blood glucose monitoring systems and laboratory blood glucose monitoring systems, are based upon amperometric, coulometric, potentiometric, voltammetric or other electrical measurement of an electro-active species produced by a reaction with an analyte such as glucose or the measurement of a direct property of the analyte matrix. A combination of these methods also can be employed for calculating an analyte concentration.

In SMBG systems, an electrochemical measurement often is performed by inserting a biosensor into a handheld meter and introducing a drop of a fluidic sample such as blood onto the biosensor that comprises a defined sample space, a dried chemical reagent and a system of electrodes. Upon detecting the sample, the meter then performs the electrical measurement, and mathematical algorithms are used to convert the results into a reliable glucose concentration.

For example, in some amperometric measurements, a test sequence is applied to a sample having an analyte of interest, where the sequence has AC potentials at different frequencies followed by a longer, fixed DC potential. A response current to the applied test sequence is monitored as the analyte is reduced or oxidized. The resulting DC current exhibits an exponential decay, as described by the Cottrell equation. As the slope of the decay decreases and approaches a constant rate of change with respect to time, the magnitude of the current can be used to quantify the analyte. The AC current is largely independent of the analyte and is more closely related to other variables such as hematocrit (Hct) and temperature.

The magnitude, rate and shape of the current decay, however, can be influenced by many variables including, but not limited to, reagent thickness, wetting of the reagent, rate of sample diffusion, Hct and temperature, as well as presence of certain interferences. These interferents, or confounding variables, can cause an increase or decrease the observed magnitude of the DC current that is proportional to an analyte such as glucose, thereby causing a deviation from the "true" glucose concentration. Efforts to combine the AC and DC current response information to generate a "true" glucose value either are extremely complex or have been largely unsatisfactory.

Current methods and systems provide some advantages with respect to convenience; however, there remains a need for alternative methods of electrochemically measuring an analyte in a fluidic sample even in the presence of confounding variables.

BRIEF SUMMARY

In view of the disadvantages noted above, the disclosure describes methods of electrochemically measuring an analyte in a fluidic sample such as a body fluid. The methods are based upon an inventive concept that includes applying a test sequence that includes at least one DC block having excitation pulses and recovery pulses and then using information derived from at least one recovery pulse to correct and/or compensate for temperature effects on an analyte concentration. For example, information such as current response, shape and/or magnitude of the recovery pulse can be used to determine the effects of temperature on the analyte concentration. Thus, there is unique information content, particularly pertaining to temperature, encoded by the recovery current responses, which provides value and can be utilized to further refine accuracy and performance of analyte testing systems The inventive concept therefore provides certain advantages, effects, features and objects when compared to known methods of measuring an analyte concentration (or value) in a fluidic sample.

In one aspect, an electrochemical analysis method is provided for measuring, determining, calculating or otherwise predicting an analyte concentration in a fluidic sample that has been applied to an electrochemical biosensor. The method can include the steps of providing a test sequence of at least one DC block to the fluidic sample and measuring the response information thereto, where the test block is designed to elicit specific information about temperature effects, where the DC block includes at least one recovery pulse, and where a closed circuit condition of an electrode system of the electrochemical biosensor is maintained during the DC block.

The at least one DC block is a continuous, pulsed excitation waveform (i.e., the potential is applied and controlled throughout the DC block in a closed circuit), which is in contrast to some pulsed amperometric methods that employ an open circuit between excitation pulses. The DC block includes a plurality of short-duration excitation pulses and recovery pulses optimized for detecting an analyte such as glucose, the optimization pertaining to pulse duration, ramped transitions between the excitation pulse and recovery pulse, number of current responses measured during each pulse, and where in each pulse current response measurements are taken. The DC block can be from at least one (1) pulse to about ten (10) pulses at a potential that alternates between about 0 mV to about +450 mV in a closed circuit. Each pulse can be applied for about 50 msec to about 500 msec. Moreover, the ramp rate can be from about 10 mV/msec to about 50 mV/msec.

In addition, the method can include a step of constructing a multivariate analysis (MVA) to build a partial least squares (PLS) regression model for temperature using response information from at least one (1) recovery pulse to correct and/or compensate for temperature effects on the analyte concentration.

One PLS regression model can use response information from at least one (1) excitation pulse and at least one (1) recovery pulse, where the model is based upon a full covariate dataset of Hct, temperature and analyte concentration. Alternatively, the PLS regression model is based upon a partial covariate dataset of temperature and analyte concentration.

In some instances, the PLS regression model also can use response information from an AC block to further correct and/or compensate for temperature effects on the analyte concentration. Thus, the test sequence also can include at least one AC block.

With respect to the AC block, it can be a plurality of low-amplitude signals applied sequentially or simultaneously in parallel. In some instances, the AC block includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies desired low-amplitude AC signals.

In some instances, the AC block is applied for about 500 msec to about 1.5 sec. In other instances, the AC block is applied for about 100 msec to about 300 msec.

In some instances, the test sequence also can include a second DC block. In other instances, the test sequence includes both the AC block and the second DC block.

In view of the foregoing, devices, apparatuses and systems used in connection with body fluid analysis are provided that incorporate one or more of the measurement methods disclosed herein. These devices, apparatuses and systems can be used to determine concentration of analytes including, but not limited to, amino acids, antibodies, bacteria, carbohydrates, drugs, lipids, markers, nucleic acids, peptides, proteins, toxins, viruses and other analytes, as well as combinations thereof. In certain instances, the analyte is glucose.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
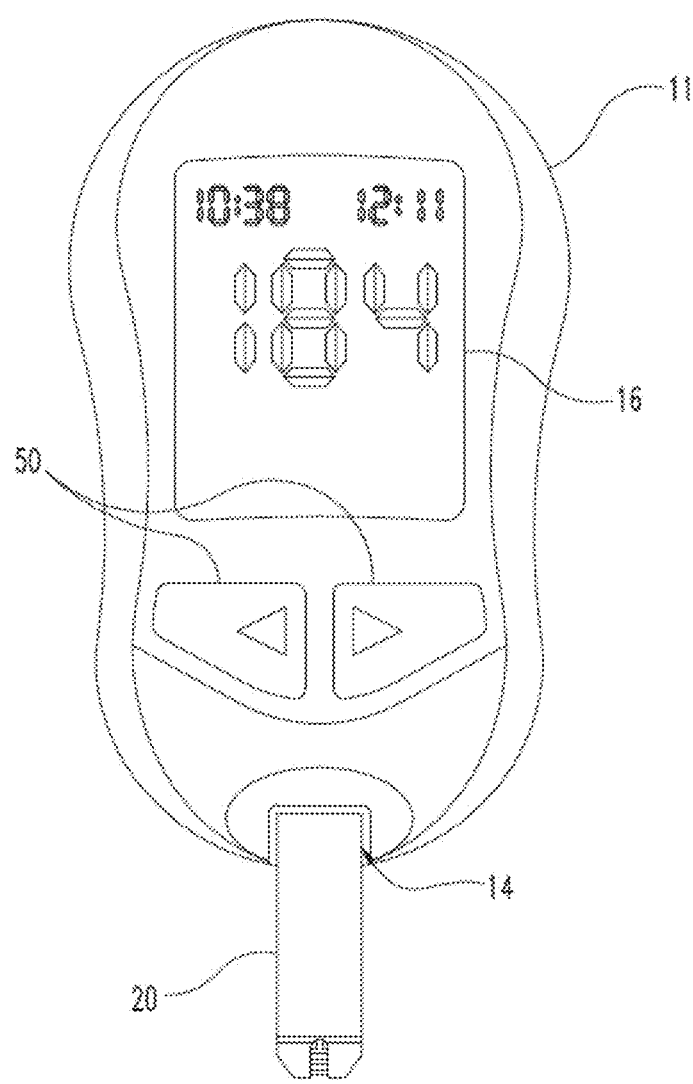
FIG. 1 shows an exemplary analyte measurement system comprising a meter and a biosensor.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments above and the claims below. Reference should therefore be made to the embodiments above and claims below for interpreting the scope of the inventive concept. As such, it should be noted that the embodiments described herein may have advantages, effects, features and objects useful in solving other problems.

DESCRIPTION OF PREFERRED EMBODIMENTS

The methods, devices, apparatuses and systems now will be described more fully hereinafter with reference to the accompanying drawings, in which some, but not all embodiments of the inventive concept are shown. Indeed, the methods, devices, apparatuses and systems may be embodied in many different forms and should not be construed as limited to the embodiments set forth herein; rather, these embodiments are provided so that this disclosure will satisfy applicable legal requirements.

Likewise, many modifications and other embodiments of the methods, devices, apparatuses and systems described herein will come to mind to one of skill in the art to which the disclosure pertains having the benefit of the teachings presented in the foregoing descriptions and the associated drawings. Therefore, it is to be understood that the methods, devices, apparatuses and systems are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, devices, apparatuses and systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

Analyte measuring methods are disclosed herein that use response information derived from at least one DC recovery pulse to provide an analyte concentration in a reliable manner, even in the presence of temperature variations. These measuring methods also can be used to reduce the effects of confounding variables such as temperature, thereby providing a more "true" analyte concentration.

The measurement methods disclosed herein largely utilize amperometry; however, it is contemplated that the methods can be used with other electrochemical measurement methods (e.g., coulometry, potentiometry or voltammetry). Additional details regarding exemplary electrochemical measurement methods are disclosed in, for example, U.S. Pat. Nos. 4,008,448; 4,225,410; 4,233,029; 4,323,536; 4,891,319; 4,919,770; 4,963,814; 4,999,582; 4,999,632; 5,053,199; 5,108,564; 5,120,420; 5,122,244; 5,128,015; 5,243,516; 5,288,636; 5,352,351; 5,366,609; 5,385,846; 5,405,511; 5,413,690; 5,437,999; 5,438,271; 5,508,171; 5,526,111; 5,627,075; 5,628,890; 5,682,884; 5,727,548; 5,762,770; 5,858,691; 5,997,817; 6,004,441; 6,054,039; 6,254,736; 6,270,637; 6,645,368; 6,662,439; 7,073,246; 7,018,843; 7,018,848; 7,045,054; 7,115,362; 7,276,146; 7,276,147; 7,335,286; 7,338,639; 7,386,937; 7,390,667; 7,407,811; 7,429,865; 7,452,457; 7,488,601; 7,494,816; 7,545,148; 7,556,723; 7,569,126; 7,597,793; 7,638,033; 7,731,835; 7,751,864; 7,977,112; 7,981,363; 8,148,164; 8,298,828; 8,329,026; 8,377,707; and 8,420,404, as well as RE36268, RE42560, RE42924 and RE42953.

Advantageously, the methods described herein can be incorporated into SMBG devices, apparatuses and systems to more accurately and quickly report an analyte concentration, such as a glucose concentration, especially a blood glucose concentration.

Moreover, these measurement methods can be implemented using advanced microprocessor-based algorithms and processes that result in dramatically improved system performance. These methods also offer flexibility and number of ways to create algorithms that can achieve improved performance such as 10/10 performance. As used herein, "10/10 performance" means that a measured bG value is within about ±10% of the actual bG value for bG concentrations>100 mg/dL, and within ±10 mg/dL of the actual bG value for bG concentrations<100 mg/dL.

Details regarding additional electrochemical measurement methods that may be useful in performing the methods disclosed herein can be found in the following co-filed and co-pending patent applications titled: "METHODS OF SCALING DATA USED TO CONSTRUCT BIOSENSOR ALGORITHMS AS WELL AS DEVICES, APPARATUSES AND SYSTEMS INCORPORATING THE SAME" (Intl Patent Application No. PCT/EP2014/054952); "METHODS OF ELECTROCHEMICALLY MEASURING AN ANALYTE WITH A TEST SEQUENCE HAVING A PULSED DC BLOCK AS WELL AS DEVICES, APPARATUSES AND SYSTEMS INCORPORATING THE SAME" (Intl Patent Application No. PCT/EP2014/054965); "METHODS OF FAILSAFING ELECTROCHEMICAL MEASUREMENTS OF AN ANALYTE AS WELL AS DEVICES, APPARATUSES AND SYSTEMS INCORPORATING THE SAME" (Intl Patent Application No. PCT/EP2014/054955); "DESCRIPTOR-BASED METHODS OF ELECTROCHEMICALLY MEASURING AN ANALYTE AS WELL AS DEVICES, APPARATUSES AND SYSTEMS INCORPORATING THE SAME" (Intl Patent Application No. PCT/EP2014/054956); and "METHODS OF DETECTING HIGH ANTIOXIDANT LEVELS DURING ELECTROCHEMICAL MEASUREMENTS AND FAILSAFING AN ANALYTE CONCENTRATION THEREFROM AS WELL AS DEVICES, APPARATUSES AND SYSTEMS INCORPORATING THE SAME" (Intl Patent Application No. PCT/EP2014/054962).

Analyte Measurement Devices, Apparatuses and Systems

Prior to, and in connection with, describing the inventive measurement methods, FIG. 1 shows an exemplary analyte measurement system including a device such as a test meter 11 operatively coupled with an electrochemical biosensor 20 (also known as a test element). Meter 11 and biosensor 20 are operable to determine concentration of one or more analytes in a fluidic sample provided to the biosensor 20. In some instances, the sample may be a body fluid sample such as, for example, whole blood, plasma, serum, urine or saliva. In other instances, the fluidic sample may be another type of sample to be tested for the presence or concentration of one or more electrochemically reactive analyte(s) such as an aqueous environmental sample.

In FIG. 1, the biosensor 20 is a single use test strip removably inserted into a connection terminal 14 of meter 11. In some instances, biosensor 20 is configured as a blood glucose test element and includes features and functionalities for electrochemically measuring glucose. In other instances, biosensor 20 is configured to electrochemically measure one or more other analytes such as, for example, amino acids, antibodies, bacteria, carbohydrates, drugs, lipids, markers, nucleic acids, peptides, proteins, toxins, viruses, and other analytes.

Meter 11 includes an electronic display 16 that is used to display various types of information to the user including analyte concentration(s) or other test results, and user interface 50 for receiving user input. Meter 11 further includes a microcontroller and associated test signal generating and measuring circuitry (not shown) that are operable to generate a test signal, to apply the signal to the biosensor 20, and to measure one or more responses of the biosensor 20 to the test signal. In some instances, meter 11 can be configured as a blood glucose measurement meter and includes features and functionalities of the ACCU-CHEK® AVIVA® meter as described in the booklet "Accu-Chek® Aviva Blood Glucose Meter Owner's Booklet" (2007), portions of which are disclosed in U.S. Pat. No. 6,645,368. In other instances, meter 11 can be configured to electrochemically measure one or more other analytes such as, for example, amino acids, antibodies, bacteria, carbohydrates, drugs, lipids, markers, nucleic acids, proteins, peptides, toxins, viruses, and other analytes. Additional details regarding exemplary meters configured for use with electrochemical measurement methods are disclosed in, for example, U.S. Pat. Nos. 4,720,372; 4,963,814; 4,999,582; 4,999,632; 5,243,516;

5,282,950; 5,366,609; 5,371,687; 5,379,214; 5,405,511; 5,438,271; 5,594,906; 6,134,504; 6,144,922; 6,413,213; 6,425,863; 6,635,167; 6,645,368; 6,787,109; 6,927,749; 6,945,955; 7,208,119; 7,291,107; 7,347,973; 7,569,126; 7,601,299; 7,638,095 and 8,431,408.

One of skill in the art understands that the measurement methods described herein can be used in other measurement devices, apparatuses, systems and environments such as, for example, hospital test systems, laboratory test systems and others.

It shall be understood that the biosensor and meter can include additional and/or alternate attributes and features in addition to or instead of those shown in FIG. 1. For example, the biosensor can be in the form of a single use, disposable electrochemical test strip having a substantially rectangular shape. It shall be appreciated that the biosensors can include different forms such as, for example, test strips of different configurations, dimensions or shapes, non-strip test elements, disposable test elements, reusable test elements, micro-arrays, lab-on-chip devices, bio-chips, bio-discs, bio-cds or other test elements. Additional details regarding exemplary biosensors configured for use with electrochemical measurement methods are disclosed in, for example, U.S. Pat. Nos. 5,694,932; 5,762,770; 5,948,695; 5,975,153; 5,997,817; 6,001,239; 6,025,203; 6,162,639; 6,245,215; 6,271,045; 6,319,719; 6,406,672; 6,413,395; 6,428,664; 6,447,657; 6,451,264; 6,455,324; 6,488,828; 6,506,575; 6,540,890; 6,562,210; 6,582,573; 6,592,815; 6,627,057; 6,638,772; 6,755,949; 6,767,440; 6,780,296; 6,780,651; 6,814,843; 6,814,844; 6,858,433; 6,866,758; 7,008,799; 7,063,774; 7,238,534; 7,473,398; 7,476,827; 7,479,211; 7,510,643; 7,727,467; 7,780,827; 7,820,451; 7,867,369; 7,892,849; 8,180,423; 8,298,401; 8,329,026, as well as RE42560, RE42924 and RE42953.

Measurement Methods

As noted above, the measurement methods described herein are based upon an inventive concept that includes using response information from a test sequence having at least one DC block, where the DC block further includes at least one recovery pulse, and where a closed circuit condition of an electrode system of the electrochemical biosensor is maintained during the DC block. Specifically, the measurement methods use response information derived from at least one recovery pulse to compensate and/or correct for confounding variables such as temperature on an analyte concentration.

Some steps in common among the methods are applying to a fluidic sample such as a body fluid sample a test sequence having at least one DC block of excitation and recovery pulses and measuring the current responses to the DC block. In other instances, the test sequence can include an AC block of low-amplitude signals in connection with the at least one DC block. In still other instances, additional AC and/or DC blocks can be included in the test sequence.

Figure 2A:
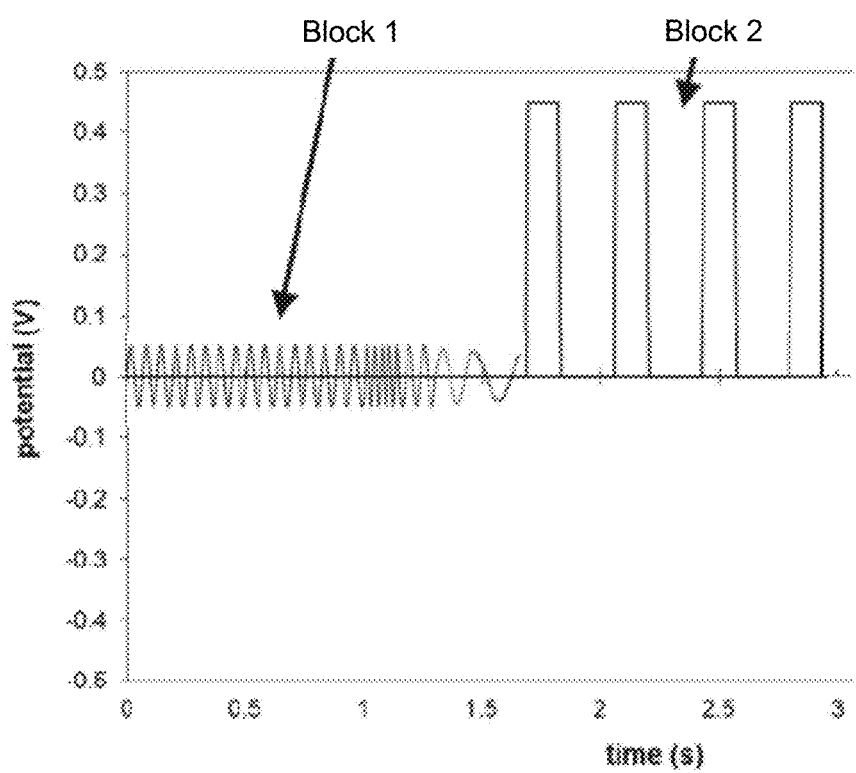
FIGS. 2A-B show exemplary test sequences that may be employed by an analyte measurement device, apparatus or system.
Figure 2B:
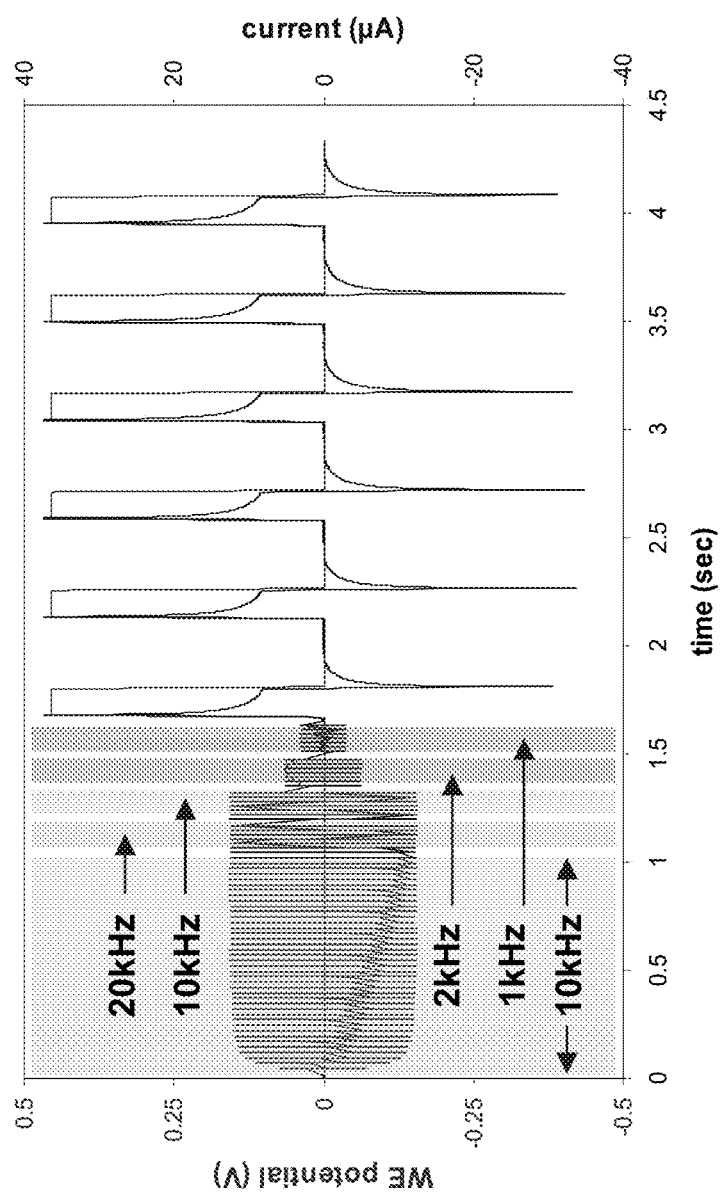
Figure 3:
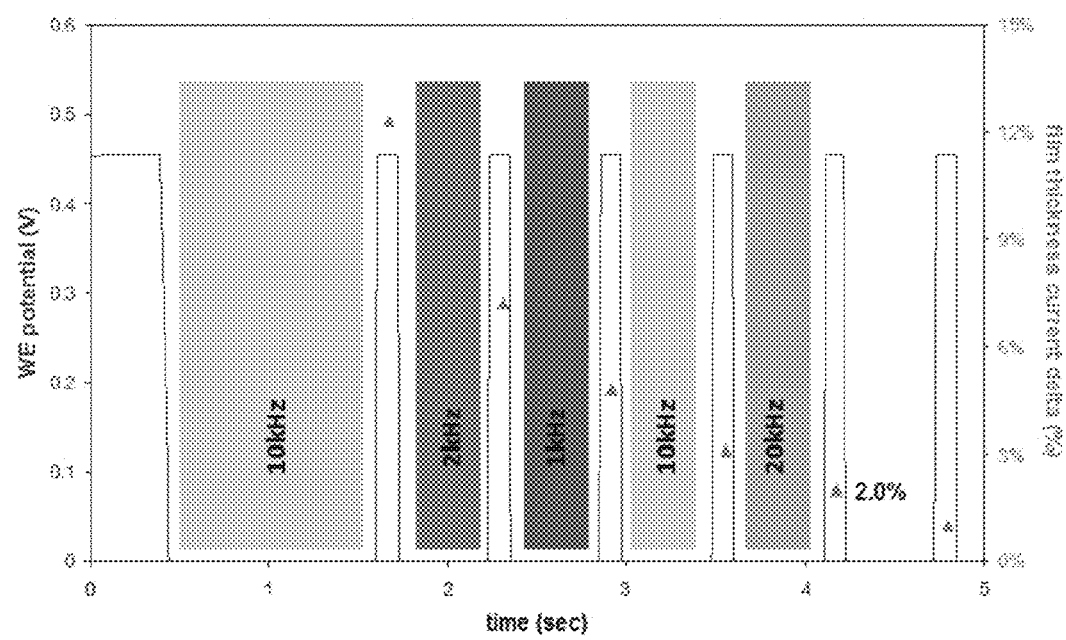
FIG. 3 shows another exemplary test sequence that may be employed by an analyte measurement device, apparatus or system.

FIGS. 2A-B show exemplary test sequences that may be used in connection with SMBG and other test systems, where the test sequences can include one or more blocks of AC and/or DC potentials. For example, the test sequence can include an AC block followed by a controlled, DC pulse profile sequence such as: (1) an AC block of a plurality low-amplitude signals; and (2) a DC block of short-duration (e.g., about 50-500 msec) about 450-mV excitation pulses separated by similarly short-duration (e.g., about 50-500 msec) recovery pulses, during which a closed circuit 0-mV recovery potential is applied.

When part of the test sequence, the AC block can include a plurality of AC segments such as, for example, from about 2 segments to about 10 segments, from about 3 segments to about 9 segments, from about 4 segments to about 8 segments, from about 5 segments to about 7 segments, or about 6 segments. In other instances, the AC block can include about 2 segments, about 3 segments, about 4 segments, about 5 segments, about 6 segments, about 7 segments, about 8 segments, about 9 segments, or about 10 segments. In still other instances, the AC block can have more than 10 segments, that is, about 15 segments, about 20 segments, or about 25 segments. In yet other instances, the AC block can include 1 segment, where the segment has multiple low-frequency AC signals applied simultaneously.

One of skill in the art understands that the number of AC segments will be limited by the complexity of the response, the associated frequency range and time available to perform the measurements. Higher frequencies generally require high bandwidth electronics and faster sampling, whereas lower frequencies take longer and are typically noisier. The maximum number of segments therefore will be a compromise of these parameters, choosing the minimum count and frequency span needed to discriminate the sample and environmental and/or interferents of interest.

As used herein, "about" means within a statistically meaningful range of a value or values such as a stated concentration, length, molecular weight, pH, potential, time frame, temperature, voltage or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The frequency of each signal in each segment of the AC block can be from about 1 kHz to about 20 kHz, from about 2 kHz to about 19 kHz, from about 3 kHz to about 18 kHz, from about 4 kHz to about 17 kHz, from about 5 kHz to about 16 kHz, from about 6 kHz to about 15 kHz, from about 7 kHz to about 14 kHz, from about 8 kHz to about 13 kHz, from about 9 kHz to about 12 kHz or from about 10 kHz to about 11 kHz. In other instances, the frequency of each segment in the AC block can be about 1 kHz, about 2 kHz, about 3 kHz, about 4 kHz, about 5 kHz, about 6 kHz, about 7 kHz, about 8 kHz, about 9 kHz, about 10 kHz, about 11 kHz, about 12 kHz, about 13 kHz, about 14 kHz, about 15 kHz, about 16 kHz, about 17 kHz, about 18 kHz, about 19 kHz, or about 20 kHz. In still other instances, the frequency of each signal in each segment of the AC block can be more than 20 kHz, that is, about 30 kHz, about 40 kHz, or about 50 kHz. In some instances, one or more of the segments can have the same frequency, whereas in other instances each segment has a distinct frequency from the other segments. Four frequencies, however, generally is adequate. The exact frequencies employed can be readily generated by simple integer division of a measurement system clock's maximum frequency.

A maximum frequency limit for a signal in a segment of the AC block, however, can be up to about 100 kHz for an inexpensive, battery-powered handheld instrument. Beyond that, the increasing demands on analog bandwidth, sampling rate, storage and processing speed quickly add up, while the imaginary portion of a typical biosensor response becomes increasingly smaller with frequency. Lower frequencies have longer periods and take longer times to sample with comparable accuracy.

The AC block typically includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies the desired low-amplitude AC signals. The AC frequencies may be applied sequentially, or combined and applied simultaneously and analyzed via Fourier Transform.

The AC block can be applied for about 500 msec to about 1.5 sec, about 600 msec to about 1.25 sec, about 700 msec to about 1 sec, or about 800 msec to about 900 msec. Alternatively, the AC block can be applied for about 500 msec, about 600 msec, about 700 msec, about 800 msec, about 900 msec, about 1 sec, about 1.25 sec or about 1.5 sec. In particular, AC block is applied for about 100 msec to about 300 msec.

One of skill in the art, however, understands that the number, frequency, duration and order of the AC segments can be varied.

AC current response information can be obtained at any time during a test sequence. Impedance results at lower frequencies may be influenced by analyte concentration if obtained after an electrochemical cell is DC polarized. In some instances, a series of AC current response measurements can be obtained early in the test sequence. Measurements taken shortly after a fluidic sample is applied to a biosensor will be influenced by diffusion, temperature and reagent solubility. In other instances, the AC response current measurements can be obtained at a sufficient time after an adequate sample has been applied to allow the response to stabilize, and avoid the transient response in the first second. Likewise, response current measurements can be made at one or more frequencies. Due to their capacitive nature, multiple AC measurements separated by a frequency octave or decade may offer different sensitivities or easier manipulation.

Additional details regarding exemplary AC blocks in electrochemical measurement methods are disclosed in, for example, U.S. Pat. Nos. 7,338,639; 7,390,667; 7,407,811; 7,417,811; 7,452,457; 7,488,601; 7,494,816; 7,597,793; 7,638,033; 7,751,864; 7,977,112; 7,981,363; 8,148,164; 8,298,828; 8,377,707 and 8,420,404.

With respect to the at least one DC block, it can include a constantly applied potential difference that alternates between about 0 mV and a predetermined positive potential difference, or other slowly time-varying potential difference that can be analyzed by traditional DC electrochemical methods. One of skill in the art, however, understands that the range for the applied potential difference can, and will, vary depending upon the analyte and reagent chemistry used.

The DC block can include a plurality of pulses such as, for example, from about 2 pulses to about 10 pulses, from about 3 pulses to about 9 pulses, from about 4 pulses to about 8 pulses, from about 5 pulses to about 7 pulses, or about 6 pulses. In other instances, the DC block can include about 2 pulses, about 3 pulses, about 4 pulses, about 5 pulses, about 6 pulses, about 7 pulses, about 8 pulses, about 9 pulses, or about 10 pulses. In still other instances, the DC block can have more than 10 pulses, that is, about 15 pulses, about 20 pulses, or about 25 pulses. As used herein, "pulse" means at least one excitation and/or one recovery period. The number of pulses, however, typically is limited by the available time for the test sequence. Shorter durations probe further from the electrode surface, and increase sensitivity to reagent thickness and diffusion modifiers.

The potential of each pulse in the DC block can be from about 0 mV to about 450 mV, from about 10 mV to about 425 mV, from about 15 mV to about 400 mV, from about 20 mV to about 375 mV, from about 25 mV to about 350 mV, from about 30 mV to about 325 mV, from about 35 mV to about 300 mV, from about 40 mV to about 275 mV, from about 45 mV to about 250 mV, from about 50 mV to about 225 mV, from about 75 mV to about 200 mV, from about 100 mV to about 175 mV, or from about 125 mV to about 150 mV. In other instances, the potential of each pulse in the DC block can be about 1 mV, about 10 mV, about 15 mV, about 20 mV, about 25 mV, about 30 mV, about 35 mV, about 40 mV, about 45 mV, about 50 mV, about 60 mV, about 70 mV, about 80 mV, about 90 mV, about 100 mV, about 110 mV, about 120 mV, about 130 mV, about 140 mV, about 150 mV, about 160 mV, about 170 mV, about 180 mV, about 190 mV, about 200 mV, about 210 mV, about 220 mV, about 230 mV, about 240 mV, about 250 mV, about 260 mV, about 270 mV, about 280 mV, about 290 mV, about 300 mV, about 310 mV, about 320 mV, about 330 mV, about 340 mV, about 350 mV, about 360 mV, about 370 mV, about 380 mV, about 390 mV, about 400 mV, about 410 mV, about 420 mV, about 430 mV, about 440 mV, or about 450 mV. In still other instances, the potential of each pulse of the DC block can be more than 450 mV, that is, about 475 mV, about 500 mV, about 525 mV, about 550 mV, about 575 mV, about 600 mV kHz, about 625 mV, about 650 mV, about 675 mV, about 700 mV, about 725 mV, or about 750 mV. In still other instances, the excitation pulse potential can be greater-than, less-than or equal to about +450 mV. In some instances, one or more of the pulses can have the same potential, whereas in other instances each pulse has a distinct potential from the other pulses.

As noted above, the applied DC potential can be fixed at about 0 mV between excitation pulses to provide a recovery pulse, thus making it a generally continuous excitation waveform. This is in contrast to a test signal sequence from known techniques that prescribe the use of an open circuit between positive DC pulses, thereby excluding the possibility of collecting and analyzing the current between positive pulses.

Regardless of the number, each DC pulse can be applied for about 50 msec to about 500 msec, about 60 msec to about 450 msec, about 70 msec to about 400 msec, about 80 msec to about 350 msec, about 90 msec to about 300 msec, about 100 msec to about 250 msec, about 150 msec to about 200 msec, or about 175 msec. Alternatively, each pulse can be applied for about 50 msec, about 60 msec, about 70 msec, about 80 msec, about 90 msec, about 100 msec, about 125 msec, about 150 msec, about 175 msec, about 200 msec, about 225 msec, about 250 msec, about 275 msec, about 300 msec, about 325 msec, about 350 msec, about 375 msec, about 400 msec, about 425 msec, about 450 msec, about 475 msec or about 500 msec. In particular, each DC pulse at +450 mV can be applied for about 250 msec, and each DC pulse at 0 mV can be applied for about 500 msec. Alternatively still, each pulse can be applied for less than about 50 msec or more than about 500 msec. The duration should be long enough or the onset soft enough to avoid charging currents. Regardless, the pulse duration should be applied long enough to enable reasonable 50/60 Hz noise rejection.

Moreover, the time between pulses is ideally long enough to allow the electrochemical cell to discharge and return close to its pre-pulse state. Furthermore, the operating potential will depend upon the mediator and measurement system. The examples herein demonstrate proof-of-principal with NA-derived redox mediator.

Generally, the ramp rate of each DC pulse is selected to provide about 50% or greater reduction in peak current relative to the peak current provided by a nearly ideal potential transition. In some instances, each pulse can have the same ramp rate. In other instances, some pulses can have the same ramp rate and other pulses can have a different ramp rate. In still other instances, each pulse has its own ramp rate. For example, effective ramp rates can be from about 5 mV/msec to about 75 mV/msec or from about 10 mV/msec to about 50 mV/msec, 15 mV/msec to about 25 mV/msec, or about 20 mV/msec. Alternatively, the ramp rate can be about 5 mV/msec, about 10 mV/msec, about 15 mV/msec, about 20 mV/msec, about 25 mV/msec, about 30 mV/msec, about 35 mV/msec, about 40 mV/msec, about 45 mV/msec, about 50 mV/msec, about 55 mV/msec, about 60 mV/msec, about 65 mV/msec, about 70 mV/msec, or about 75 mV/msec. In particular, the ramp rate can be from about 40 mV/msec to about 50 mV/msec.

Like the AC block, one of skill in the art understands that the number, potential, duration and order of the DC pulses can be varied.

In the methods, the AC and/or DC response current information can be obtained (i.e., measured or recorded) at about 2,000/sec to about 200,000/sec, at about 3,000/sec to about 190,000/sec, at about 4,000/sec to about 180,000/sec, at about 5,000/sec to about 170,000, at about 6,000/sec to about 160,000/sec, at about 7,000/sec to about 150,000/sec, at about 8,000/sec to about 140,000/sec, at about 9,000/sec to about 130,000/sec, at about 10,000/sec to about 120,000/sec, at about 15,000/sec to about 110,000/sec, at about 20,000/sec to about 100,000/sec, at about 30,000/sec to about 90,000/sec, at about 40,000/sec to about 80,000/sec, at about 50,000/sec to about 70,000/sec, or at about 60,000/sec. In some instances, the AC and/or DC response current information can be obtained at about 100/sec to about 200/sec, at about 200/sec to about 300/sec, at about 300/sec to about 400/sec, at about 400/sec to about 500/sec, at about 500/sec to about 600/sec, at about 600/sec to about 700/sec, at about 700/sec to about 800/sec, at about 800/sec to about 900/sec, at about 1,000/sec to about 1,500/sec, at about 1,500/sec to about 2,000/sec, at about 2,000/sec to about 2,500/sec, at about 2,500/sec to about 3,000/sec, at about 3,000/sec to about 3,500/sec, at about 3,500/sec to about 4,000/sec, at about 4,000/sec to about 4,500/sec, at about 4,500/sec to about 5,000/sec, at about 5,000/sec to about 5,500/sec, at about 5,500/sec to about 6,000/sec, at about 6,000/sec to about 6,500/sec, at about 6,500 to about 7,000/sec, at about 7,000/sec to about 7,500/sec, at about 7,500/sec to about 8,000/sec, at about 8,000/sec to about 8,500/sec, at about 8,500 to about 9,000/sec, at about 9,000/sec to about 9,500/sec, at about 9,500/sec to about 10,000/sec, at about 10,000/sec to about 20,000/sec, at about 20,000/sec to about 30,000/sec, at about 30,000/sec to about 40,000/sec, at about 40,000/sec to about 50,000/sec, at about 50,000/sec to about 60,000/sec, at about 60,000/sec to about 70,000/sec, at about 70,000/sec to about 80,000/sec, at about 80,000/sec to about 90,000/sec, at about 90,000/sec to about 100,000/sec, at about 100,000/sec to about 110,000/sec, at about 110,000/sec to about 120,000/sec, at about 120,000/sec to about 130,000/sec, at about 130,000/sec to about 140,000/sec, at about 140,000/sec to about 150,000/sec, at about 150,000/sec to about 160,000/sec, at about 160,000/sec to about 170,000/sec, at about 170,000/sec to about 180,000/sec, at about 180,000/sec to about 190,000/sec, or at about 200,000/sec. In other instances, the AC and/or DC response current information can be obtained up to about 100/sec, about 200/sec, about 300/sec, about 400/sec, about 500/sec, 600/sec, about 700/sec, about 800/sec, about 900/sec, about 1,000/sec, about 1,250/sec, about 1,500/sec, about 1,750/sec, about 2,000/sec, about 2,225/sec, about 2,500/sec, about 2,750/sec, about 3,000/sec, about 3,250/sec, about 3,500/sec, about 3,750/sec, about 4,000/sec, about 4,250/sec, about 4,500/sec, about 4,750/sec, about 5,000/sec, about 5,250/sec, about 5,500/sec, about 5,750/sec, about 6,000/sec, about 6,250/sec, about 6,500, about 7,000/sec, about 7,250/sec, about 7,500/sec, about 7,750/sec, about 8,000/sec, about 8,250/sec, about 8,500/sec, about 8,750, about 9,000/sec, about 9,250/sec, about 9,500/sec, about 9,750/sec, about 10,000/sec, about 15,000/sec, about 20,000/sec, about 25,000/sec, about 30,000/sec, about 35,000/sec, about 40,000/sec, about 45,000/sec, about 50,000/sec, about 55,000/sec, about 60,000/sec, about 65,000/sec, about 70,000/sec, about 75,000/sec, about 80,000/sec, about 85,000/sec, about 90,000/sec, about 95,000/sec, about 100,000/sec, about 105,000/sec, about 110,000/sec, about 115,000/sec, about 120,000/sec, about 125,000/sec, about 130,000/sec, about 135,000/sec, about 140,000/sec, about 145,000/sec, about 150,000/sec, about 155,000/sec, about 160,000/sec, about 165,000/sec, about 170,000/sec, about 175,000/sec, about 180,000/sec, about 185,000/sec, about 190,000/sec, about 195,000 or at about 200,000/sec. In yet other instances, the AC and/or DC response current information can be obtained at more than 200,000/sec.

AC and/or DC current response information can be collected from the test sequence and includes current responses to the AC and DC blocks. In some instances, the current response information can be collected at an A/D sampling rate for DC and AC measurements to simplify the system design, including a single shared signal path for AC and DC measurements. Common digital audio sampling rates range include, but are not limited to, from about 44.1 kHz to about 192 kHz. A/D converters in this range are readily available from variety of commercial semiconductor suppliers.

A more detailed test sequence is shown in FIG. 2B, where the one trace illustrates the applied DC potential, and the other trace illustrates the AC and DC current responses, respectively. In this example, the applied DC potential can be fixed at 0 mV between pulses to provide the recovery pulse, thus making it a generally continuous excitation waveform. This is in contrast to a test sequence from known techniques that prescribe the use of an open circuit between positive DC pulses, thereby excluding the possibility of collecting and analyzing the current between positive pulses.

As used herein, "recovery pulse" or "recovery potential pulse" means a zero-potential pulse applied for an adequately long recovery period in which the electrochemical reaction with the analyte of interest (e.g., glucose) is turned "off," thereby allowing the system to return to a fixed starting point before subsequent interrogation with another positive DC excitation pulse.

Just as the shapes of the current decays from positive DC excitation pulses encode information about glucose, Hct and temperature (as well as other SMBG strip processes), the shapes of the recovery pulses also are unique. Each DC recovery pulse produces a negative current response with a rate of growth that also encodes distinct, time-ordered information describing how the biamperometric system returns to a given reference state. The rate of current growth during the recovery pulse is not simply a mirror image of the current decay associated with a neighboring positive DC excitation pulse, because the glucose reaction has been turned off by selecting a potential magnitude that cannot initiate and sustain the electrochemical reaction with glucose. The measurement methods disclosed herein utilize unique information content pertaining to temperature and other confounding variables encoded by the recovery current responses to improve the accuracy and performance of analyte test systems such as SMBG systems.

In the measurement methods below, a DC block, similar to that illustrated in FIG. 2B, was used to analyze various concentrations of blood samples. An experimental design was used to systematically vary glucose, Hct and temperature levels. In this covariate dataset, the target glucose levels were 40, 120, 200, 350 and 500 mg/dL; the Hct target levels were 10, 24, 42, 56 and 70%; and the target temperature levels were 6, 12, 24, 32 and 44° C., respectively. The resulting dataset contained 1966 samples (observations). The data were collected using an environmental chamber, and the SMBG meters and strips were given ample time to equilibrate to each target temperature before use. Therefore, the reported meter temperatures closely corresponded with the actual chamber temperatures. Reference values for glucose and Hct were obtained and verified through independent analytical measurements.

The data were analyzed using a partial least squares (PLS) regression, which is a multivariate technique that also may be referred to as projection to latent structures. PLS regression considers the covariance between a group of explanatory (independent) variables, herein termed X-variables, and one or more response (dependent) variables, herein referred to as Y-variables. Unlike multiple linear regression, PLS can be used when there are a large number of X-variables per observation, when there are more X-variables than observations, and/or when the X-variables are correlated. Explained simply, the PLS procedure forms new variables, or factors, that are linear combinations of the original X-variables and uses them for predictors of the Y variable(s). The factors are selected to describe the greatest variability in the X-matrix that also correlates with the variation in the Y-variable(s). Here, PLS regression was performed using the Simca®-P+ Software Package (Umetrics, Inc.; Kinnelon, N.J.). PLS models were constructed using the DC current values as the X-variables and the recorded meter temperature as the response, or Y-variable. PLS models with only one Y-variable are often referred to as PLS1 models. All X and Y variables were independently centered and scaled to unit variance before analysis.

Figure 4:
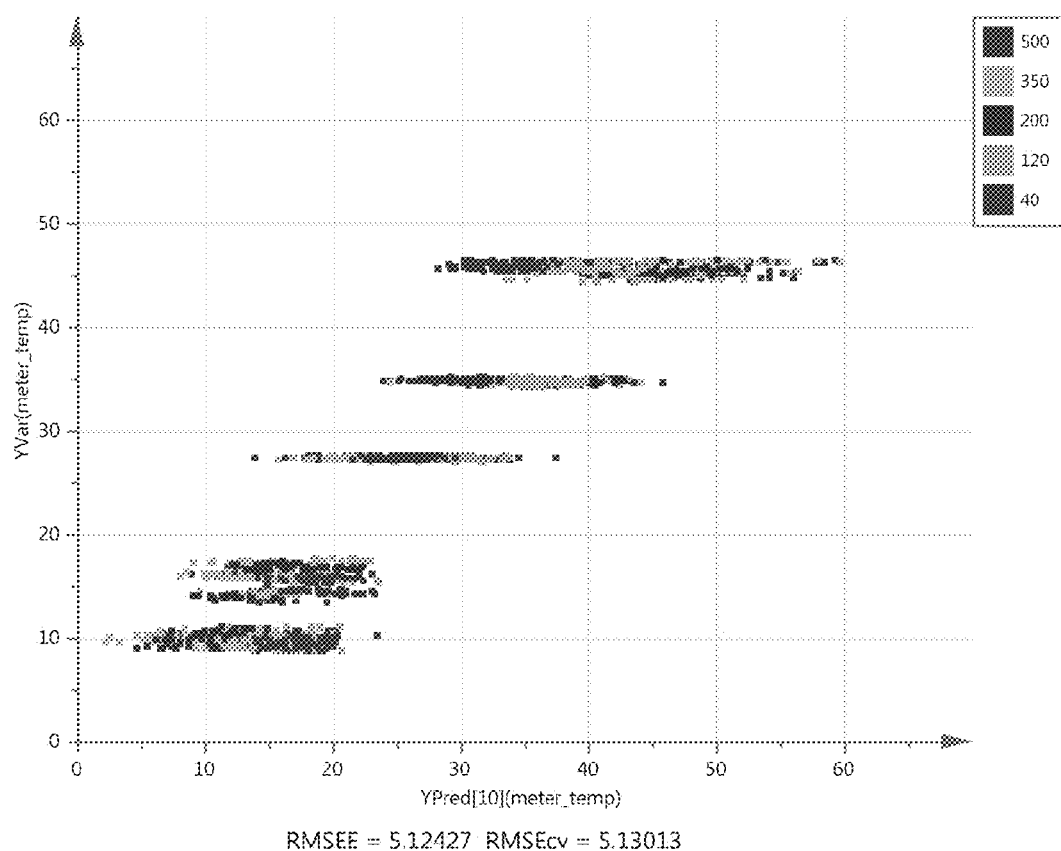
FIG. 4 is a graph showing actual admittance values (y-axis) vs. predicted admittance values (x-axis) for a PLS model.

A first PLS model (PLS Model 1) was constructed using the full covariate dataset (all glucose, Hct and temperature levels, 1966 observations) There were 796 X-variables, consisting of the current values from the first four (4) positive DC excitation pulses and the first three (3) recovery pulses. The PLS analysis yielded ten (10) significant factors, which were able to describe 84.3% (measured as $R^2Y$) of the variability in temperature. The standard deviation of the Y-residuals was 5.11° C., and the root-mean-squared-error-of-estimate (RMSEE) of the model, used as a measure of precision, was 5.12° C. A plot of the actual Y values versus the predicted Y values is shown in FIG. 4. Observations are colored according to target glucose level as denoted in the legend at the upper right of FIG. 4.

Figure 5:
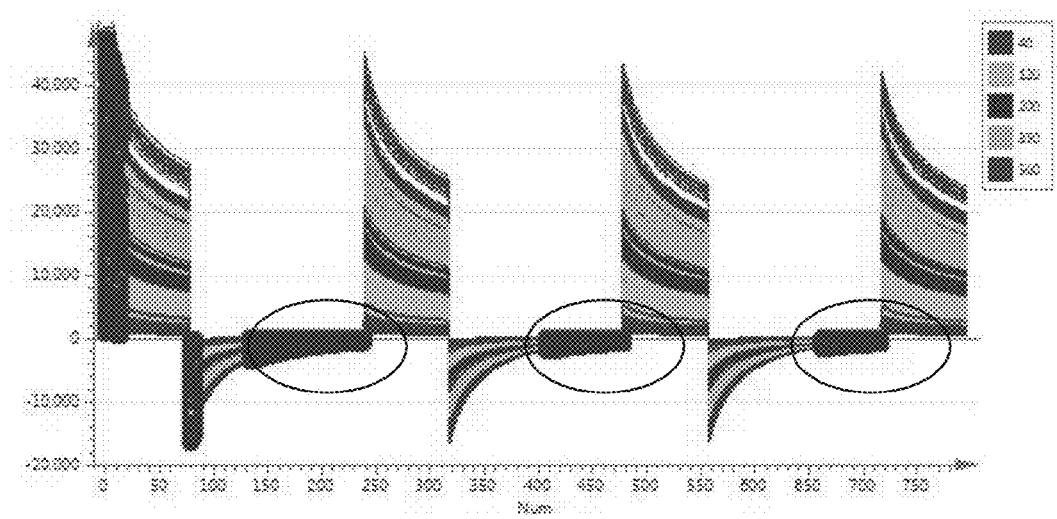
FIG. 5 is a graph showing DC current responses for a plurality of covariate dataset observations colored by target glucose level wherein the y-axis is the current response in nA, the x-axis is the number of the DC current value in the time series, and the DC currents circled correspond to X-variables with the highest VIP scores.

The most significant X-variables in PLS Model 1, in terms of their individual contributions to overall model performance, were identified using a statistic called the variable influence on projection (VIP). The normalized VIP score provides a way to compare X-variables and rank them in order of importance in the model. As shown in FIG. 5, most of the X-variables with the highest VIP scores are from the recovery pulses, thus showing that the recovery pulse currents contain unique and useful information for modeling temperature. All 1966 observations are shown in FIG. 5 and are colored by target glucose level.

For comparison, a second PLS Model (PLS Model 2) was constructed using the full covariate dataset; however, the X-variables consisted of 316 current values from the first four (4) DC positive pulses only. The first three (3) recovery pulses (which were included in PLS Model 1) were intentionally omitted as a second confirmation of unique temperature information in the recovery pulse current responses. PLS Model 2 yielded four (4) significant factors, which were able to describe 80% ($R^2Y$) of the variability in temperature. The standard deviation of the Y-residuals was 5.77° C., and the RMSEE of the model was also 5.77° C. Comparing PLS Model 1 to Model 2, there is an apparent improvement of 11.3% in the RMSEE, thus confirming that the information from the recovery pulse current adds unique temperature information that is not available in the positive DC excitation pulse current responses alone.

The PLS models for temperature also were designed to compensate for changing Hct level, which was co-varied with temperature. To verify that a combined temperature-Hct effect did not play a role in the VIP-based selection of significant variables in Model 1 or the improvement in RMSEE observed between the two PLS models, a second analogous set of PLS models for temperature was created using a reduced dataset. The reduced dataset was a subset of the covariate dataset and contained a total of 394 observations from all glucose and temperature level combinations—but only at the nominal Hct level (42%).

Figure 6:
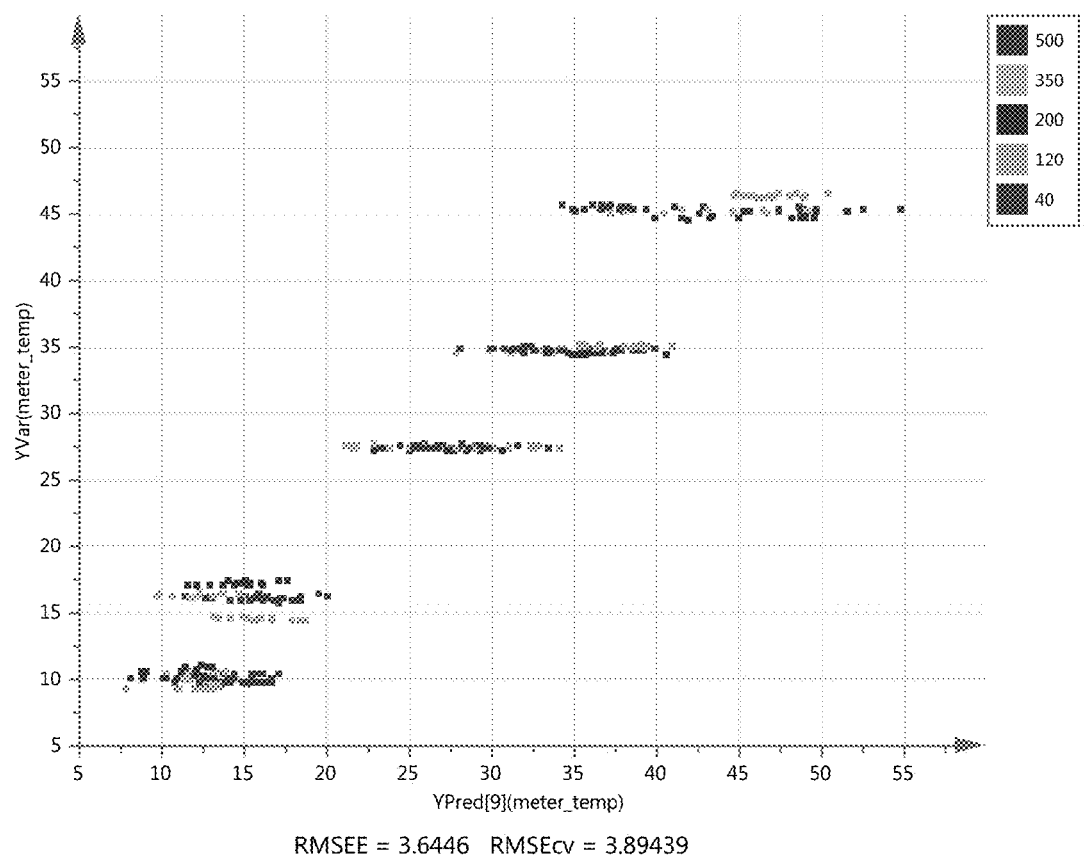
FIG. 6 is a graph showing actual admittance values (y-axis) vs. predicted admittance values (x-axis) for another PLS model.

As such, a third PLS model (PLS Model 3) was constructed using the reduced dataset and 796 X-variables, consisting of the current values from the first four (4) DC positive pulses and the first three (3) recovery pulses. As above, the recorded meter temperature from the covariate data was used as the Y-variable. The PLS analysis yielded nine (9) significant factors, which were able to describe 92.0% ($R^2Y$) of the variability in temperature. The standard deviation of the Y-residuals was 3.60° C., and the RMSEE of the model was 3.64° C. A plot of the actual Y values versus the predicted Y values is shown in FIG. 6. Observations are colored according to target glucose level.

Figure 7:
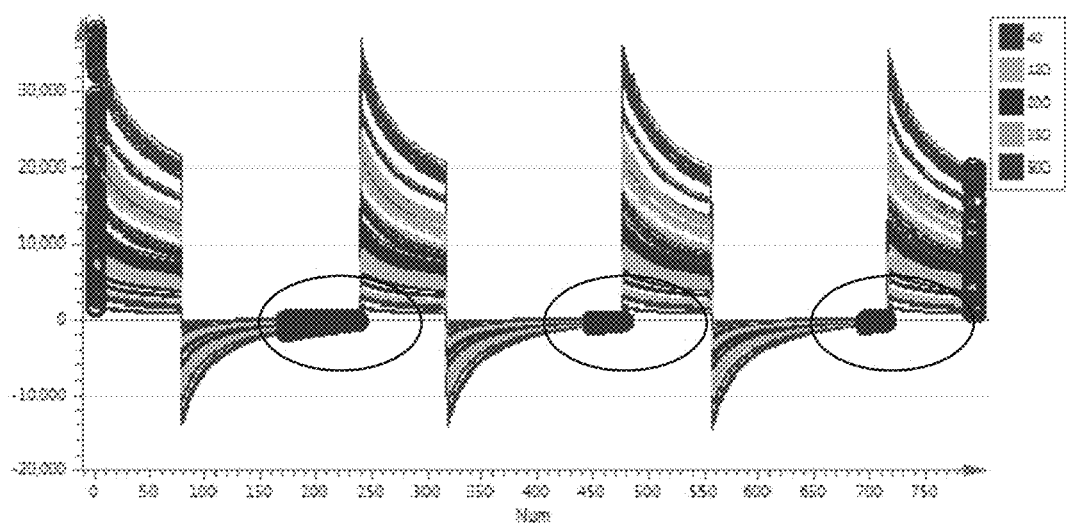
FIG. 7 is a graph showing DC current responses for a plurality of covariate dataset observations colored by target glucose level wherein the y-axis is the current response in nA, the x-axis is the number of the DC current value in the time series, and the DC currents circled correspond to X-variables with the highest VIP scores.

As with PLS Model 1, the most significant X-variables in PLS Model 3, in terms of their individual contributions to overall model performance, were identified using the VIP metric. As shown in FIG. 7, most of the X-variables with the highest VIP scores are from the recovery pulses, again confirming that the recovery pulse currents contain unique and useful information for modeling temperature. All 394 observations are shown in FIG. 7 and are colored by target glucose level. DC current responses for the 394 observations in the reduced data set are colored by target glucose level. The y-axis is the current response in nA, and the x-axis is the number of DC current value in the time series. Those DC currents highlighted in red correspond to X-variables with the highest VIP scores.

For comparison, a fourth PLS model (PLS Model 4) was built using the reduced data set; however, like PLS Model 2, the X-variables consisted of 316 current values from the first four (4) DC positive pulses only. The first three (3) recovery pulses (which were included in PLS Model 3) were intentionally omitted to confirm unique information content in the recovery pulse current responses. The PLS analysis for Model 4 yielded eight (8) significant factors, which were able to describe 91% ($R^2Y$) of the variability in temperature. The standard deviation of the Y-residuals was 3.81° C., and the RMSEE of the model was 4.02° C. Comparing PLS Model 3 and Model 4, there is an apparent improvement of 9.5% in the RMSEE, again confirming that the information from the recovery pulse current adds unique temperature information that is not available in the positive DC current responses alone.

It should be appreciated that an SMBG algorithm that combines AC and DC information would make it difficult to de-convolve how much of the observed temperature compensation is from the AC information alone or from the DC recovery current responses alone. To demonstrate the value of the recovery pulse current information in a way that was independent AC information. However, it was also deemed necessary to also evaluate whether the X-variables from the recovery pulse current responses were still identified as being useful to a PLS temperature model if AC information was available simultaneously. Therefore, an additional PLS model—which did include the AC information—was constructed and evaluated.

Figure 8:
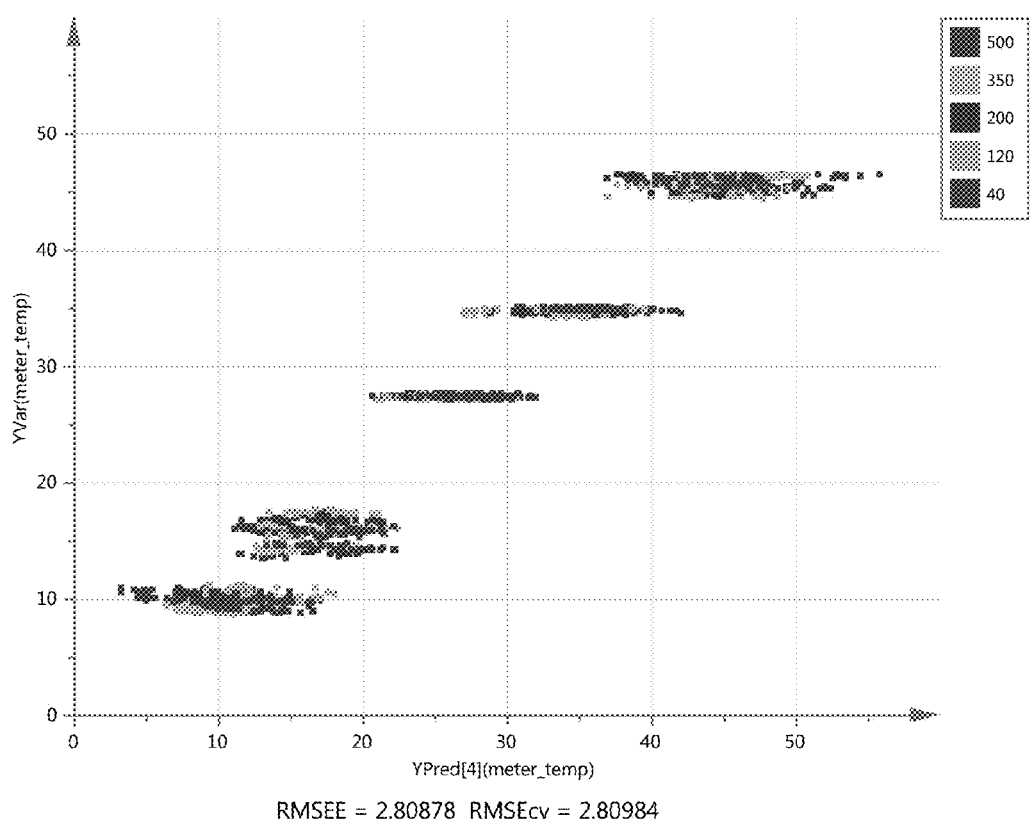
FIG. 8 is a graph showing actual admittance values (y-axis) vs. predicted admittance values (x-axis) for another PLS model.

As such, and for a direct comparison with PLS Model 1, a fifth PLS model (PLS Model 5) was constructed using the full covariate dataset (1966 observations); however, eight (8) AC variables, consisting of phase and admittance measurements at four (4) different AC frequencies, were added to the 796 X-variables, which consisted of the current values from the first four (4) DC positive pulses and the first three (3) recovery pulses. As above, the recorded meter temperature from the covariate data was used as the Y-variable. The PLS analysis yielded four (4) significant factors, which were able to describe 95.3% ($R^2Y$) of the variability in temperature. The standard deviation of the Y-residuals was 2.80° C., and the RMSEE of the model was 2.81° C. A plot of the actual Y values (y-axis) versus the predicted Y values (x-axis) is shown in FIG. 8. Observations are colored according to target glucose level.

Figure 9:
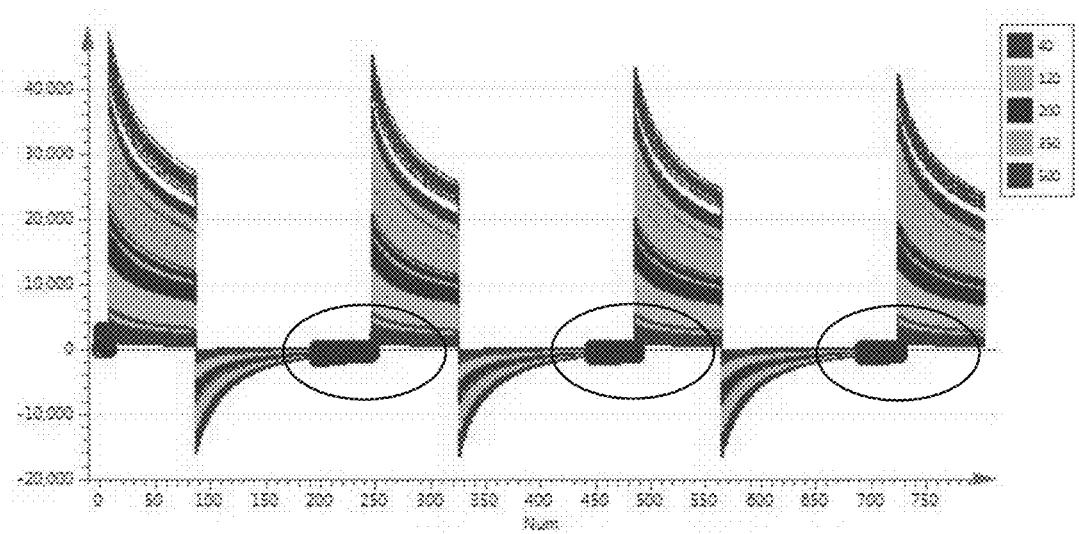
FIG. 9 is a graph showing DC current responses for a plurality of covariate dataset observations colored by target glucose level wherein the y-axis is the current response in nA, the x-axis is the number of the DC current value in the time series, and the DC currents circled correspond to X-variables with the highest VIP scores.

The VIP metric then was used to identify the most significant X-variables in PLS Model 5, in terms of their individual contributions to overall model performance. As shown in FIG. 9, the X-variables with the highest VIP scores are the AC variables (shown before the first DC positive pulse response) and X-variables from the recovery pulses. All 1966 observations are shown in FIG. 9 and are colored by target glucose level the x-axis is the current response in nA, and the y-axis is the number of DC current value in the time series. X-variables highlighted in red have the highest VIP scores.

PLS Model 5 shows optimal results for temperature were obtained using the AC information combined with information from the DC recovery pulse current responses. Because the variables from the recovery pulse current responses had significant VIP scores, this confirms that they are still adding unique and valuable information to the temperature prediction. Since the AC data contained excellent information about Hct and temperature, it is not surprising that the best PLS prediction of temperature is obtained by combining the AC variables and DC recovery pulse current variables.

There are several significant observations that can be made from the foregoing evaluations. First, the selection of significant variables from PLS Models 1 and 3 show definitively that there is unique information content, pertaining particularly to temperature, encoded by the recovery pulse responses. Second, the comparison of PLS Models 1 and 2, as well as PLS Models 3 and 4, show that including recovery pulse currents in temperature models improves the RMSEE of the temperature predictions. Third, the two sets of PLS models show that the VIP-selected variables and the observed improvement in RMSEE comes from a true ability to model temperature and that the observed relationships are not confounded by changing Hct level. And finally, the confirmation study with AC information shows that X-variables from the DC recovery current responses are important and still add unique information to the temperature prediction model, even when AC information is present.

The results from PLS regression modeling showed definitively that there is unique information content, including information of sample temperature, encoded by the recovery pulse responses. A comparison of appropriate models also confirmed that the inclusion of recovery pulse currents in quantitative PLS models improves the ability to predict temperature. The PLS analyses were structured to show that the improvement is based upon an enhanced ability to model temperature, specifically and to verify that the results are not confounded by other co-varying parameters, such as changing Hct level. A summary of the PLS models is provided in the table below.

TABLE 1

PLS Model Summary.

| Model | Predictors | Y | Data |
|---|---|---|---|
| PLS Model 1 | Positive and negative DCs | Meter temperature | Full covariate |
| PLS Model 2 | Positive DCs | Meter temperature | Full covariate |
| PLS Model 3 | Positive and negative DCs | Meter temperature | Nominal Hct |
| PLS Model 4 | Positive DCs | Meter temperature | Nominal Hct |
| PLA Model 5 | Positive and negative DCs and AC | Meter temperature | Full covariate |

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A method of compensating for temperature while electrochemically measuring an analyte in a fluid sample, the method comprising the steps of:
   applying an electrical test sequence to an electrochemical biosensor, the biosensor comprising:
   an electrode system,
   a reagent in electrical communication with the electrode system, and
   a receptacle configured to contact the fluid sample provided to the biosensor with the reagent,
   with the fluid sample in fluidic contact with the reagent, wherein the test sequence comprising at least one direct current (DC) block having a sequence of at least one excitation potential pulse and at least one recovery potential pulse, wherein a closed circuit condition of the electrode system is maintained during the DC block; and determining the analyte concentration based upon current response information from the DC block, wherein information from the at least one recovery potential pulse is used to compensate for temperature effects on the analyte concentration based upon a partial least squares (PLS) regression model.

2. The method of claim 1, wherein the at least one excitation potential pulse is about +450 mV and the at least one recovery potential pulse is about 0 mV, and wherein each pulse is from about 50 msec to about 500 msec.

3. The method of claim 1 further comprising:
measuring current response information to the at least one excitation potential pulse and to the at least one recovery potential pulse; and
determining the analyte concentration from the excitation current response and the recovery current response.

4. The method of claim 1, wherein the test sequence further comprises an alternating current (AC) block of low-amplitude signals of at least two different frequencies.

5. The method of claim 4, wherein the AC block is applied before the at least one DC block, after the at least one DC block or interspersed within the at least one DC block.

6. The method of claim 1, wherein the PLS regression model is based upon a covariate dataset comprising hematocrit, temperature and analyte concentration.

7. The method of claim 1, wherein the PLS regression model is based upon a covariate dataset comprising temperature and analyte concentration.

8. The method of claim 4, wherein the wherein the frequencies are about 10 kHz, about 20 kHz, about 10 kHz, about 2 kHz and about 1 kHz, and wherein each is applied for about 0.5 seconds to about 1.5 seconds.

9. The method of claim 1, wherein the information of an electrical response to a relaxation pulse includes unique information not found in information of an electrical response to an excitation pulse.

10. The method of claim 1, wherein the analyte concentration is a glucose concentration.

\* \* \* \* \*